United States Patent [19]

Rodder

[11] 4,163,390

[45] Aug. 7, 1979

[54] BIPOLAR FLUID MEASURING APPARATUS

[76] Inventor: Jerome A. Rodder, 774 Sunshine Dr., Los Altos, Calif. 94022

[21] Appl. No.: 809,302

[22] Filed: Jun. 23, 1977

Related U.S. Application Data

[63] Continuation-in-part of Ser. No. 787,467, Apr. 14, 1977, abandoned.

[51] Int. Cl.$^2$ .............................................. G01F 1/68
[52] U.S. Cl. .................... 73/204; 73/205 R; 73/755
[58] Field of Search ............. 73/196, 202, 204, 205 R, 73/755

[56] References Cited

U.S. PATENT DOCUMENTS

| 3,312,106 | 4/1967 | Davis | 73/203 X |
| 3,452,595 | 7/1969 | Auger | 73/196 X |
| 3,691,830 | 9/1972 | Tomota et al. | 73/194 |

FOREIGN PATENT DOCUMENTS 2236691  7/1972  Fed. Rep. of Germany ............. 73/212

*Primary Examiner*—Herbert Goldstein
*Attorney, Agent, or Firm*—Christie, Parker & Hale

[57] ABSTRACT

In a spirometer, a breath transmission passage has first and second ends open to the atmosphere and a restriction between the first and second ends. An elongated conduit has a first port at one end, a second port at the other end, and a third port intermediate to the first and second ports to form a first flow measurement passage in the conduit between the first and third ports and a second flow measurement passage in the conduit between the second and third ports. The first end of the breath transmission passage at a point near the restriction is interconnected to the first port, and the second end of the breath transmission passage at a point near the restriction is interconnected to the second port. A source of bias gas is connected to the third port. The difference between the rate of gas flow through the first and second flow measurement passages responsive to inhalation from the exhalation to the breath transmission passage is sensed to provide a bipolar indication thereof. First and second hot wires are bent in half to extend side by side along the length of a cavity. At one end, the first and second hot wires are electrically connected to each other to form in effect a single hot wire equal in length to the first and second hot wires.

4 Claims, 4 Drawing Figures

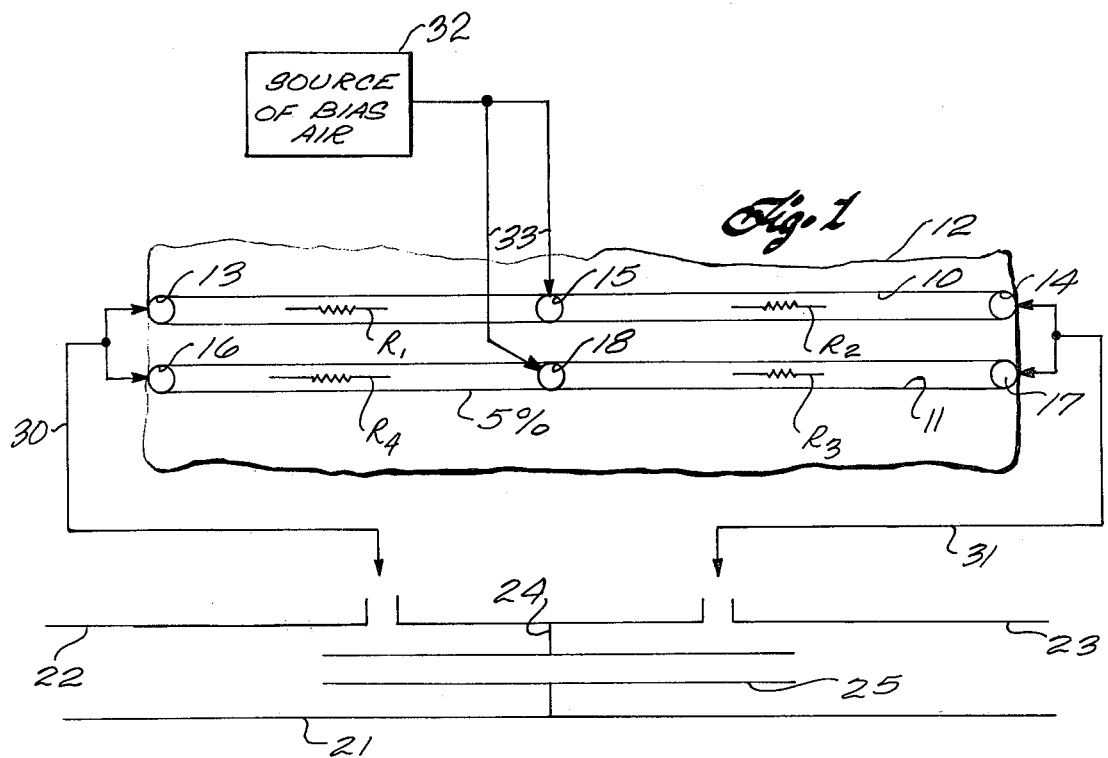
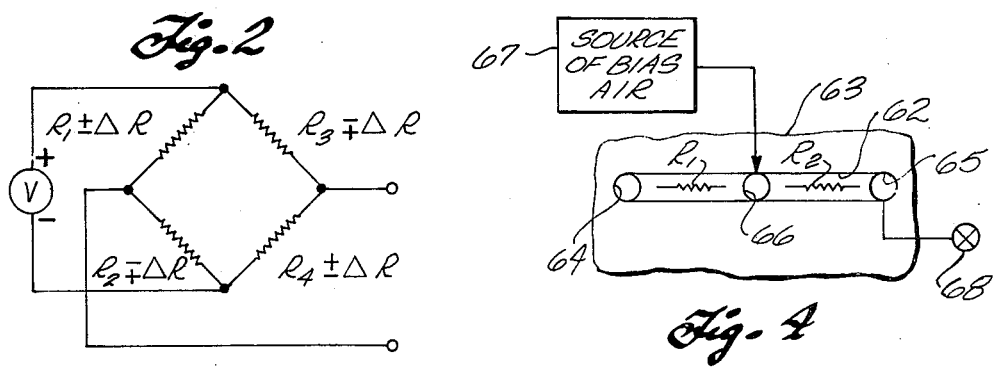
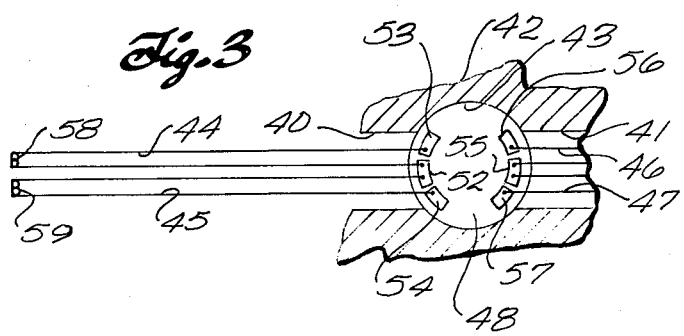

BIPOLAR FLUID MEASURING APPARATUS

CROSS REFERENCE TO RELATED APPLICATIONS

This is a continuation-in-part of my application Ser. No. 787,467, filed Apr. 14, 1977, now abandoned.

BACKGROUND OF THE INVENTION

This invention relates to apparatus for measuring bipolar fluid flow and, more particularly, to such apparatus especially well suited for use as a spirometer or pressure sensor.

My U.S. Pat. No. 3,735,752 which issued May 29, 1973, discloses a spirometer comprising a breath transmission passage in which a venturi is formed, and a flow measurement passage that communicates at one end with the throat of the venturi and at the other end with the atmosphere. Air flow through the breath transmission passage creates a subatmospheric pressure at the throat of the venturi to aspirate air from the atmosphere through the flow measurement passage. Apparatus such as a thermistor bead or a hot wire electrically connected into one arm of a bridge circuit measures the flow rate through the flow measurement passage, which is dependent upon the flow rate through the breath transmission passage. Bias air is preferably supplied to the breath transmission passage to insure that the moisture from the patient's breath does not reach the flow rate measuring apparatus in the flow measurement passage. Such moisture would have a deleterious affect on the accuracy of the measurement and would corrode a hot wire.

In the described spirometer, the flow of breath through the breath transmission passage draws air from the atmosphere through the flow measurement passage irrespective of the direction of flow through the breath transmission passage to cool the hot wire or thermistor. As a result, the electrical output from the bridge circuit does not distinguish between inhalation and exhalation.

SUMMARY OF THE INVENTION

According to the invention, hot wires are used to sense the difference between the characteristics of gas flow through flow measurement passages in a manner that increases the effective length of the hot wires without increasing the physical size of the package housing the hot wires. First and second hot wires are bent in half to extend side by side along the length of each passage. At one end, the first and second hot wires are connected to each other to form in effect a single hot wire equal in length to the first and second hot wires. The hot wires in each flow measurement passage function as one arm of an electrical bridge that provides an output representative of the gas characteristics being measured.

BRIEF DESCRIPTION OF THE DRAWINGS

The features of specific embodiments of the best mode contemplated of carrying out the invention are illustrated in the drawings, in which:

FIG. 1 is a schematic diagram of a spirometer incorporating principles of the invention;

FIG. 2 is an electrical schematic diagram depicting the electrical connections of the hot wires in the spirometer of FIG. 1;

FIG. 3 is a top sectional view of a portion of two of the flow measurement passages of FIG. 1 depicting the hot wires therein; and FIG. 4 is a schematic diagram of a pressure sensor incorporating principles of the invention.

DETAILED DESCRIPTION OF THE SPECIFIC EMBODIMENTS

In FIG. 1, an elongated conduit 10 and an elongated conduit 11 are formed in a housing 12 made of a material having high thermal conductivity such as aluminum or steel to make the apparatus thermally stable. Conduit 10 has ports 13 and 14 at its ends, and a port 15 midway between ports 13 and 14 to form a pair of flow measurement passages. Conduit 11 has ports 16 and 17 at its ends, and a port 18 midway between ports 16 and 17 to form another pair of flow measurement passages. A blow tube or breath transmission passage 21 has ends 22 and 23 open to the atmosphere. Midway between ends 22 and 23, a partition 24 extends across breath transmission passage 21. A tube 25 having a substantially smaller diameter than breath transmission passage 21, passes through partition 24 to provide communication between ends 22 and 23. Tube 25 serves as a restriction on air flow between ends 22 and 23.

End 22 of breath transmission passage 21 is interconnected to ports 13 and 16 by flexible tubing designated 30, and end 23 of breath transmission passage 21 is interconnected to ports 14 and 17 by flexible tubing designated 31. Preferably, tubing 30 and 31 open into breath transmission passage 21 near the restriction, i.e. between the ends of tube 25 and partition 24 as illustrated in FIG. 1, where the gas velocity is low and thus the turbulance is small.

A source 32 of bias air under pressure is connected to ports 15 and 18 by flexible tubing designated 33. Source 32 supplies air at a sufficiently high, preferably constant, flow rate to prevent flow from breath transmission passage 21 through conduits 10 and 11 when a patient breathes through breath tramsmission passage 21.

Conduits 10 and 11 form in effect a fluid bridge comprising as a first arm the flow measurement passage between ports 15 and 13, as a second arm the flow measurement passage between ports 18 and 16, as a third arm the flow measurement passage between ports 15 and 14, and as a fourth arm the flow measurement passage between ports 18 and 17. In the absence of air flow through breath transmission passage 21, the fluid bridge is balanced, i.e., the same rate of bias air from source 32 flows through each flow measurement passage.

When a patient exhales into end 22 of breath transmission passage 21, there is a pressure drop from end 22 to end 23 by virtue of the restriction provided by tube 25. Consequently, the pressure at ports 13 and 16 rises to unbalance the fluid bridge. The bias air flowing through the flow measurement passages between ports 15 and 13 and ports 18 and 16 decreases, and the bias air flowing through the flow measurement passages between ports 15 and 14 and ports 18 and 17 increases.

When the patient inhales from end 22 of breath transmission passage 21, there is a pressure drop from end 23 to end 22 by virtue of the restriction provided by tube 25. Consequently, the pressure at ports 14 and 17 rises to unbalance the fluid bridge. The bias air flowing through the flow measurement passages between ports 15 and 14 and ports 18 and 17 decreases and the bias air flowing through the flow measurement passages between ports 15 and 13 and ports 18 and 16 increases.

Exhalation into end 23 of breath transmission passage 21 produces the same effect as inhalation from end 22, and inhalation from end 23 from breath transmission passage 21, produces the same effect as exhalation into end 22.

Breath transmission passage 21, tube 25, conduits 10 and 11, and tubing 30 and 31 are designed so there is substantially more flow resistance presented by the flow path through conduits 10 and 11 than the flow path through tube 25. For example, in the absence of bias air, about 95 percent of the gas flowing into end 22 or end 23 flows through tube 25, and about 5 percent thereof flows through conduits 10 and 11. To increase the flow rate to which the apparatus of FIG. 1 responds, it is simply necessary to substitute a tube having a larger diameter for tube 25.

To measure the flow rate of air passing through tube 25 in response to patient breathing through breath transmission passage 21, the difference between the rate of gas flow through the flow measurement passages between ports 15 and 14 and ports 18 and 17, and the flow measurement passages between ports 15 and 13 and ports 18 and 16 is sensed. Preferably, hot wires designated $R_1$, $R_2$, $R_3$, and $R_4$ in FIG. 1 are employed as sensors. Hot wire $R_1$ extends along the length of the flow measurement passage between ports 15 and 13, hot wire $R_2$ extends along the length of the flow measurement passage between ports 15 and 14, hot wire $R_3$ extends along the length of the flow measurement passage between ports 18 and 17, hot wire $R_4$ extends along the length of the flow measurement passage between ports 18 and 16.

As shown in FIG. 2, hot wires $R_1$ through $R_4$ serve as arms of an electrical bridge. Hot wires $R_1$ and $R_2$ are connected in series between the output terminals of a voltage source V, with hot wire $R_1$ connected to the positive output terminal and hot wire $R_2$ connected to the negative output terminal. Hot wires $R_3$ and $R_4$ are connected in series between the output terminals of voltage source V with hot wire $R_3$ connected to the positive output terminal and hot wire $R_4$ connected to the negative output terminal. The output of the bridge appears between the junction of hot wires $R_1$ and $R_2$ and the junction of hot wires $R_3$ and $R_4$. Air flow through breath transmission passage 21 changes the resistance to each of hot wires $R_1$ through $R_4$, as represented by $\Delta R$ in FIG. 2. As represented by the plus and minus signs in FIG. 2, the resistance of hot wires $R_1$ and $R_4$ changes in the same direction, and the resistance of hot wires $R_2$ and $R_3$ changes in the same direction and in the opposite direction from the resistance of hot wires $R_1$ and $R_4$. Specifically, responsive to patient exhalation into end 22 of breath transmission passage 21, the resistance of hot wires $R_1$ and $R_4$ increases because of the decreased flow rate of bias air through the flow measurement passages in which such hot wires are located, and the resistance of hot wires $R_2$ and $R_3$ decreases because of the increased bias flow rate through the flow measurement passages in which such hot wires are located. This produces a signal of positive polarity across the output terminals of the bridge referenced to the lower output terminal. Conversely, responsive to patient inhalation from end 22 of breath transmission passage 21, the resistance of hot wires $R_1$ and $R_4$ decreases, and the resistance of hot wires $R_3$ and $R_2$ increases. This produces a signal of negative polarity across the output terminals of the bridge referenced to the lower output terminal. In summary, the hot wires in all four arms of the bridge operate in push-pull fashion to produce a large signal in response to air flow through breath transmission passage 21. Such signal is representative in polarity and magnitude to the direction of such flow and the rate of such flow, respectively.

With one exception, the apparatus of FIG. 1 is preferably constructed in the manner disclosed in my copending application, Ser. No. 787,468, filed Apr. 14, 1977, and entitled FLUID MEASURING APPARATUS. The disclosure of that application is incorporated herein by reference. As depicted in FIG. 3 herein, elongated cavities 40 and 41 are formed in a housing 42. Cavities 40 and 41 extend in axial alignment in opposite directions from a cylindrical chamber 43 in housing 42. Chamber 43 has a cylindrical axis transverse to the axes of cavities 40 and 41. Thin elongated, i.e., uncoiled, hot wires 44 and 45, which are bent in half, extend side by side along the length of cavity 40. Similarly, thin elongated hot wires 46 and 47 extend side by side along the length of cavity 41. A circular disc-shaped printed circuit board 48 for supporting and electrically connecting the ends of hot wires 44 through 47 fits in chamber 43. Printed circuit board 48 has an electrically insulative substrate on which electrically conductive coaxial arcuate pads 52, 53, 54, 55, 56 and 57 are deposited. Solder connections are formed between the pads and the ends of the hot wires. The one exception to the construction of the above referenced application is that the two hot wires in the same cavity, e.g., hot wires 44 and 45 in cavity 40, and hot wires 46 and 47 in cavity 41, are electrically connected in series, rather than one hot wire from each cavity. Specifically, pad 52 interconnects hot wires 44 and 45 at one end to form in effect a single hot wire, e.g., $R_1$, equal in length to hot wires 44 and 45. At the other end, hot wire 44 is connected to a pad 53 and hot wire 45 is connected to a pad 54. Pad 55 interconnects hot wires 46 and 47 at one end to form in effect a single hot wire, e.g., hot wire $R_2$, equal in length to hot wires 46 and 47. At the other end, hot wire 46 is connected to a pad 56 and hot wire 47 is connected to a pad 57. As shown by pairs of rods 58 and 59 for hot wires 44 and 45, respectively, the middle of each hot wire is supported by a pair of rods made of a nonconductive resilient material such as quartz. Each rod pair is anchored at one end and free to move at the other end. The free end of each rod pair is deformed, i.e., deflected, toward circuit board 48, so such rod functions as a spring to exert tension on the middle of the corresponding hot wire to keep such hot wire taut as its length changes. Preferably, the rods of each pair are spaced apart a distance that maintains the two halves of the corresponding hot wire precisely parallel to each other. Relating the structure of FIG. 3 to FIG. 1, cavities 40 and 41 form conduit 10, port 15 opens into chamber 43, port 13 opens into cavity 40 adjacent to the middle of hot wires 44 and 45, and port 14 opens into cavity 41 adjacent to the middle of hot wires 46 and 47. The same structure disclosed in FIG. 3 is provided for the other two hot wires, e.g., $R_3$ and $R_4$. Pads, 53, 54, 56 and 57, and the comparable pads for the other two hot wires are electrically connected to form the bridge disclosed in FIG. 2. By utilizing this construction, a hot wire having an effective length four times as long as the cavity is formed. This provides very high sensitivity.

As an alternative to the arrangement disclosed in FIGS. 1 and 3, which provides a faster response at the expense of sensitivity, a single conduit is provided rather than two conduits. Two hot wires, which are bent in half, extend side by side along each flow measurement passage of the single conduit. This arrangement is identical to that disclosed in FIG. 3 except that the two side by side hot wires are not interconnected at one end. Thus, the two side by side hot wires in one flow measurement passage serve as hot wires $R_1$ and $R_4$ in the bridge of FIG. 2, and the two side by side hot wires in the other flow measurement passage serve as hot wires $R_2$ and $R_3$ in the bridge of FIG. 2.

FIG. 4 illustrates a pressure sensor. A conduit 62 is formed in housing 63. Ports 64 and 65 are located at the ends of conduit 62 and a port 66 is located midway between ports 64 and 65, to form a pair of flow measurement passages between ports 64 and 66 and ports 65 and 66. Port 64 is connected by a needle valve 68 to a region at a pressure to be sensed to expose port 64 to the pressure to be sensed. Port 65 is connected by an adjustable needle valve 69 to the atmosphere to expose port 65 to a constant pressure. A source of bias air 67 is connected to port 66 to supply air at a pressure higher than the pressure to be sensed and at constant flow rate to the flow measurement passages. Hot wires $R_1$ and $R_4$ of the bridge of FIG. 2 are disposed between ports 66 and 64 and hot wires $R_2$ and $R_3$ are disposed between ports 66 and 65. Alternatively, the four hot wires could be disposed in separate flow measurement passages as shown in FIG. 1. Valves 68 and 69 are adjusted to balance the bridge output, i.e., to make the bridge output signal zero, with atmospheric pressure in the region to be sensed. The degree to which valves 68 and 69 are open depends on the range of pressure to be sensed. As the pressure to be sensed increases above atmospheric, the ratio of the air flow rate in the flow measurement passage between ports 64 and 66 to the air flow rate in the flow measurement passage between ports 65 and 66 decreases, and visa versa.

Alternatively, if only pressure above atmospheric is to be measured, valve 68 can be eliminated and port 64 can be directly connected to the region to be sensed. In this case, valve 69 is adjusted so the ratio of the air flow rate in the flow measurement passage between ports 64 and 66 to the air flow rate in the flow measurement passage between ports 65 and 66 is large at atmospheric pressure in the region to be sensed and decreases as the pressure increases above atmospheric.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention. For example, although use of hot wires in each arm of the bridge is preferable, simple bridge balancing resistors could be substituted for hot wires $R_3$ and $R_4$. Alternatively, instead of hot wires, bead type thermistors could be employed, or some other means for sensing the difference in fluid flow rate through the arms of the fluid bridge. The whole system could be pressurized by placing tube 21 in series with a pressurized line rather than having ends 22 and 23 open to the atmosphere.

What is claimed is:

1. Fluid measuring apparatus comprising:
 a housing having an elongated cavity enclosed on its sides;
 a first thin elongated hot wire bent in half to extend along the length of the cavity away from a junction;
 a second thin elongated hot wire bent in half to extend along the length of the cavity away from the junction in the same direction as the first hot wire so the first and second hot wires are side by side in the cavity;
 first means at the junction for supporting the ends of each hot wire in spaced electrically isolated relationship from each other and connecting one end of the first and second hot wires to each other to form in effect a first single hot wire equal in length to the first and second hot wires;
 second means spaced along the length of the cavity from the junction for supporting the middle of the first hot wire to exert tension thereon as the length of the first hot wire changes;
 third means spaced along the length of the cavity from the junction aside of the second supporting means for supporting the middle of the second hot wire to exert tension thereon as the length of the second hot wire changes;
 means for forming in the housing a fluid entrance to the cavity;
 means for forming in the housing a fluid exit from the cavity longitudinally spaced from the entrance so the hot wires lie between the entrance and the exit; and
 means for measuring the change in resistance of the hot wires.

2. The fluid measuring apparatus of claim 1, additionally comprising:
 a second elongated cavity enclosed on its sides in the housing and extending away from the junction in the opposite direction from the first named cavity;
 a third thin elongated hot wire bent in half to extend along the length of the second cavity away from the junction;
 a fourth thin elongated hot wire bent in half to extend along the length of the second cavity away from the junction in the same direction as the third hot wire so the third and fourth hot wires are side by side in the second cavity;
 fourth means at the junction for supporting the ends of each of the third and fourth hot wires in spaced electrically isolated relationship from each other and connecting one end of the third and fourth hot wires to each other to form in effect a second single hot wire equal in length to the third and fourth hot wires;
 fifth means spaced along the length of the second cavity from the junction for supporting the middle of the third hot wire to exert tension thereon as the length of the third hot wire changes;
 sixth means spaced along the length of the second cavity from the junction aside of the fifth supporting means for supporting the middle of the fourth hot wire to exert tension thereon as the length of the fourth hot wire changes;
 means for forming in the housing a fluid entrance to the second cavity; and
 means for forming in the housing a fluid exit from the second cavity longitudinally spaced from the entrance so that third and fourth hot wires lie between the entrance and the exit.

3. The fluid measuring apparatus of claim 2, in which the measuring means comprises:
 first and second bridge balancing resistors;
 a source of electrical excitation energy having first and second outputs;
 means for connecting the first single hot wire and the first resistor in series with the first single hot wire connected to the first output terminal and the first resistor connected to the second output terminal; and means for connecting the second single hot wire and the second resistor in series with the second resistor connected to the first output terminal and the second single hot wire connected to the second output terminal, whereby the first and second single hot wires and the first and second resistors form a bridge having an output between the junction of the first single hot wire and the first resistor and the junction of the second single hot wire and the second resistor.

4. The fluid measuring apparatus of claim 3, in which the first and fourth supporting means comprise:

a printed circuit board having first, second, and third electrically conductive pads located side by side adjacent to the first named cavity, fourth, fifth, and sixth electrically conductive pads located side by side adjacent to the second cavity;

means for electrically connecting one end of the first hot wire to the first pad;

means for electrically connecting one end of the second hot wire to the third pad;

means for electrically connecting the other end of each of the first and second hot wires to the second pad;

means for electrically connecting one end of the third hot wire to the fourth pad;

means for electrically connecting one end of the fourth hot wire to the sixth pad; and means for electrically connecting the other end of each of the third and fourth hot wires to the second pad.

* * * * *